US012702446B2

(12) United States Patent
Işin et al.

(10) Patent No.: US 12,702,446 B2
(45) Date of Patent: Aug. 11, 2026

(54) UNILATERAL EXTERNAL FIXATOR APPARATUS AND CONTROL METHOD

(71) Applicants: Şehmuz Işin, Istanbul (TR); Baran Işin, Istanbul (TR); Ikbal Işin, Istanbul (TR)

(72) Inventors: Şehmuz Işin, Istanbul (TR); Baran Işin, Istanbul (TR); Ikbal Işin, Istanbul (TR)

( * ) Notice: Subject to any disclaimer, the term of this patent is extended or adjusted under 35 U.S.C. 154(b) by 0 days.

(21) Appl. No.: 19/331,544

(22) Filed: Sep. 17, 2025

(65) Prior Publication Data

US 2026/0013906 A1 Jan. 15, 2026

Related U.S. Application Data

(62) Division of application No. 18/470,978, filed on Sep. 20, 2023, now Pat. No. 12,433,641.

(51) Int. Cl.

*A61B 17/66* (2006.01)
*A61B 17/56* (2006.01)
*G06T 17/00* (2006.01)

(52) U.S. Cl.

CPC .............. *A61B 17/66* (2013.01); *A61B 17/56* (2013.01); *G06T 17/00* (2013.01); *A61B 2017/564* (2013.01); *G06T 2207/30008* (2013.01)

(58) Field of Classification Search

CPC . A61B 17/66; A61B 2017/681; A61B 17/683; A61B 17/56; A61B 2017/564; G06T 2207/00; G06T 17/00

See application file for complete search history.

(56) References Cited

U.S. PATENT DOCUMENTS

| | | | | |
|---|---|---|---|---|
| 1,367,578 | A | 2/1921 | Ziegler | |
| 5,728,095 | A | 3/1998 | Taylor | |
| 5,941,879 | A | 8/1999 | Walulik | |
| 5,971,984 | A | 10/1999 | Taylor | |
| 7,449,023 | B2 | 11/2008 | Walulik | |
| 8,366,710 | B2 | 2/2013 | Hirata et al. | |
| 8,388,619 | B2 | 3/2013 | Mullaney | |
| 9,642,649 | B2 * | 5/2017 | Nikonovas | G16H 20/40 |
| 10,010,346 | B2 | 7/2018 | Edelhauser | |
| 10,194,944 | B2 | 2/2019 | Edelhauser | |
| 10,194,994 | B2 * | 2/2019 | Deno | A61B 5/7221 |
| 10,258,377 | B1 | 4/2019 | Lavi | |
| 10,470,800 | B2 * | 11/2019 | Bordeaux | A61B 17/62 |
| 11,304,757 | B2 * | 4/2022 | Gutmann | G16H 20/40 |

(Continued)

FOREIGN PATENT DOCUMENTS

| | | | |
|---|---|---|---|
| EP | 0814714 | B1 | 1/1998 |
| EP | 3069673 | B1 | 9/2016 |

(Continued)

*Primary Examiner* — Eduardo C Robert
*Assistant Examiner* — Holly Joanna Lane
(74) *Attorney, Agent, or Firm* — Hayes Soloway P.C.

(57) ABSTRACT

A method of correcting a bone deformity or reducing a bone fracture with an external fixator. The method comprises uploading a first set of x-rays to a computer program, characterizing geometry of a bone deformity with the program, recommending frame geometry for correcting the deformity, then after surgery uploading a second set of x-rays with fixator attached, characterizing geometry again, calculating fixator adjustments necessary to align bones, and providing proposed fixator positions.

16 Claims, 11 Drawing Sheets

(56) References Cited

U.S. PATENT DOCUMENTS 11,334,997 B2 * 5/2022 Gutmann ............... G16H 30/40
11,337,732 B2 5/2022 Lavi
11,439,436 B2 * 9/2022 Gutmann ............. A61B 17/645
2006/0229604 A1 10/2006 Olsen et al.
2010/0234844 A1 * 9/2010 Edelhauser ............ A61B 17/62
606/56
2013/0201212 A1 * 8/2013 Haskell ................... G06T 19/00
345/632
2016/0022314 A1 1/2016 Bordeaux et al.
2021/0153944 A1 5/2021 Nikonovas
2021/0366118 A1 * 11/2021 Campbell ............... G06T 19/20

FOREIGN PATENT DOCUMENTS

WO 2012102685 A1 8/2012
WO 2014142703 A1 9/2014
WO 2023038595 A1 3/2023

* cited by examiner 150
152
154
156
158
160
162
164
166

UNILATERAL EXTERNAL FIXATOR APPARATUS AND CONTROL METHOD

CROSS-REFERENCE TO RELATED APPLICATIONS AND PRIORITY

This patent application is a Divisional of U.S. patent application Ser. No. 18/470,978 filed Sep. 20, 2023. This patent application is incorporated by reference in its entirety.

BACKGROUND OF THE INVENTION

Field of the Invention

The invention is in the field of external fixators for gradual and controlled correcting broken bones and other bone deformities.

Description of the Related Art

In various orthopedic surgical procedures, it is necessary to secure two bone portions in a relatively fixed relationship to each other. The need for establishing such secured relationship is often a result of a bone fracture or other type of bone deformity. To ensure that the bone can regenerate in the proper orientation and fuse the fracture, it is important that the bone portions be fixed in the desired position during bone regeneration.

Various external fixators for the correction of bone deformities are known. For example, U.S. Pat. No. 7,449,023 B2 to Walulik et al. discloses a method and apparatus for external fixation and correction of bone using a unilateral fixator. However, using this apparatus is difficult for complex deformities in three dimensions. Surgeons have difficulty foreseeing the bone position in a plane other than that being corrected. For example, one can correct angulation on a frontal plane, and then the bone goes somewhere else on a sagittal plane.

Another example is EP 0814714 B1 to Taylor et al. Taylor teaches a circular fixator having two rings and six struts. It solves some of the problems of Walulik, but causes other problems for surgeons and patients. The hardware is complex and surgeons have difficulty seeing the surgical area due to the struts around the patient's extremity, and it is difficult to manage all the components, which include rings, struts, anchoring elements, and more, during surgery. Patients have difficulty carrying such a bulky device on their extremity. Adjusting strut lengths every day is not easy because at least three struts are outside of the patient's view. Femoral surgeries are very uncomfortable for the patient because the patient cannot get the legs close to one another, which greatly affects the patient's daily life.

What is needed, therefore, is an external fixator that does not have the problems of prior art apparatuses. The fixator should be controllable in multiple planes, positions should be foreseeable to the surgeons, the apparatus should not be bulky and difficult to use in daily life.

SUMMARY OF THE INVENTION

The present invention is a unilateral external fixator ("UEF") and method of controlling the fixator that satisfies these needs. The apparatus comprises a central body connected to a first base and a second base via respective universal joints. Two angulation adjustment screw assemblies control geometrical position between the central body and the first base. Two additional angulation adjustment screw assemblies control geometrical position between the central body and the second base. A first axial adjustment screw in the first base adjusts axial position of a first bone attachment base. A second axial adjustment screw in the second base adjusts axial position of a second bone attachment base.

A method of correcting a bone deformity comprises the steps of providing an external fixator, uploading a first set of x-ray images prior to surgery to a computer software program, characterizing the geometry of a bone deformity with the program, recommending a frame type, shape, and geometry of the external fixator for correcting the deformity. The method further comprises the steps of, after surgery uploading a second set of x-ray images with the fixator attached, characterizing the geometry again, sending the geometry to a correction algorithm of the program, calculating fixator adjustments necessary to align bone segments, providing visualization of aligned bone segments and proposed fixator positions for user approval, and providing a correction animation in three dimensions for correcting the bone deformity using the external fixator. These and other benefits, features, and advantages will be made clearer in the accompanying description, claims, and drawings.

DETAILED DESCRIPTION OF THE INVENTION

The apparatus of the present invention is made for fixating fractured bones while making it possible to precisely adjust the relative position and orientation to the needs. The facture could be caused by a trauma or an osteotomy during surgery. The unilateral external fixator ("UEF") offers a very tight package and a wide range of adjustment positions. The challenge, however, is given by the non-linear behavior of the system. The adjustment screws do not correspond to linear motion as in a cartesian motion system. A linear movement, or any movement, requires the simultaneous change of multiple adjustment screws. The numerical method of the present invention achieves desired motion and control both position and orientation.

The UEF is given in two different configurations. The first, basic version allows the manipulation of a given bone structure in five degrees of motion. In particular, it supplies three perpendicular translations and two rotations. The extended, second version of the UEF carries an additional revolute joint, and therefore allows the manipulation of all six degrees of freedom. The method of the invention supplies a numerical solution to control both the position and the orientation of attached bone structures using the UEF.

Figure 1:
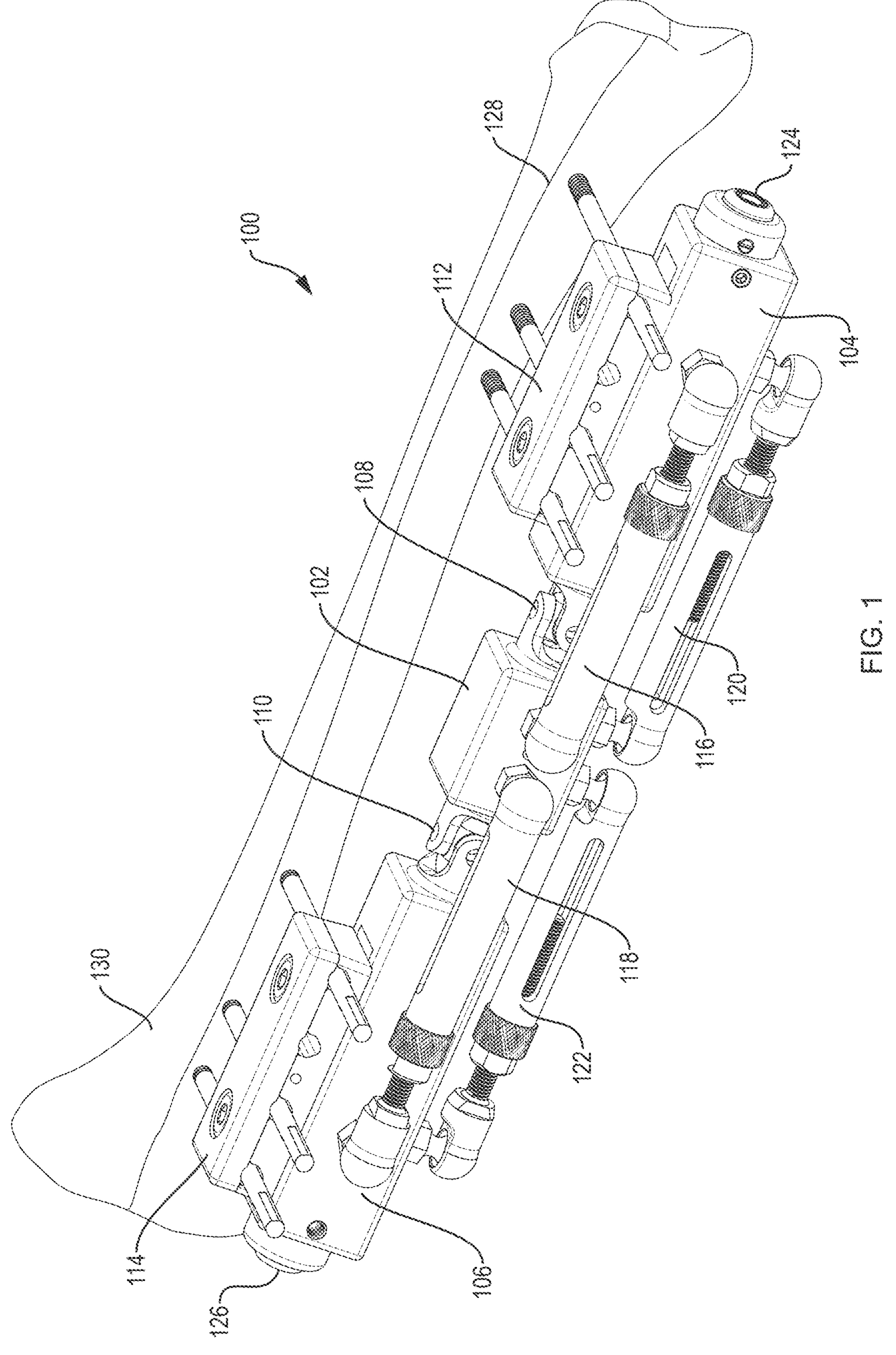
FIG. 1 is a perspective view of a first embodiment of the apparatus of the present invention.

FIG. 1 is a perspective view of a first embodiment of the UEF of present invention, providing five degrees of motion. The UEF assembly 100 comprises a central body 102 and a first base 104 in operative communication with the central body 102 via a first joint 108 disposed on a central body first side. The first joint can be a universal joint or a ball and socket joint. FIG. 1 shows it as a universal joint. A first bone attachment base 112 is fixed to a first longitudinal plane of the first base 104 for attaching the fixator to a lower bone or lower bone mockup 128. A first angulation adjustment screw assembly 116 is connected at a first end to the central body 102 and connected at a second end to the first base 104 along a longitudinal plane orthogonal to the first bone attachment base 112. A third angulation adjustment screw assembly 120 is connected at a first end to the central body 102 at a position orthogonal to that of the first angulation adjustment screw assembly 116 and connected at a second end to the first base 104 at a position orthogonal to that of the first angulation adjustment screw assembly 116. A first axial adjustment screw assembly 124 is in communication with the first base 104 that adjusts translation of the bone attachment 112 along a longitudinal axis of the first base 104.

A second base 106 is in operative communication with the central body 102 via a second joint 110 disposed on a central body second side opposite the central body first side. Like the first joint, the second joint 110 can be a universal joint or a ball and socket joint. FIG. 1 shows it as a universal joint. A second bone attachment base 114 is fixed to a first longitudinal plane of the second base 106 for attaching the fixator to an upper bone or upper bone mockup 130. A second angulation adjustment screw assembly 118 is connected at a first end to the central body 102 and connected at a second end to the second base 106 along a longitudinal plane orthogonal to the second bone attachment base 114. A fourth angulation adjustment screw assembly 122 is connected at a first end to the central body 102 at a position orthogonal to that of the second angulation adjustment screw assembly 118 and connected at a second end to the second base 106 at a position orthogonal to that of the second angulation adjustment screw assembly 118. A second axial adjustment screw 126 is in communication with the second base 106 that adjusts translation of the second bone attachment base 114 along a longitudinal axis of the second base 106.

Figure 2:
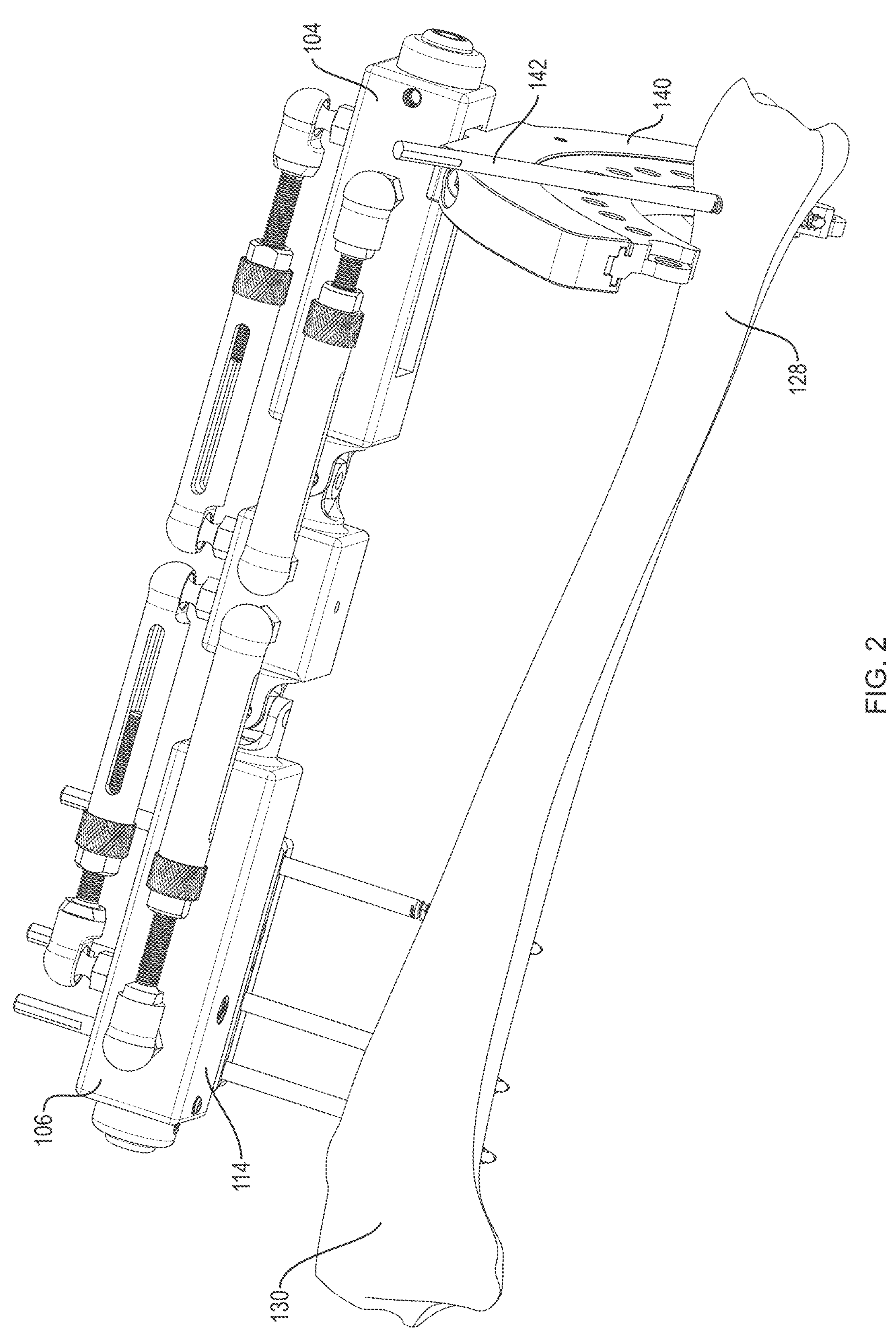
FIG. 2 is a perspective view of a second embodiment of the apparatus of the present invention.

FIG. 2 is a perspective view of a second embodiment of the UEF of present invention, providing six degrees of motion. The UEF assembly of FIG. 2 differs from that of FIG. 1 by replacing the first bone attachment base of FIG. 1 with a rotator assembly 140 fixed to the first base 104. A linking member 142 is adjustably attached to the rotator assembly 140 for attaching to the lower bone 128.

Figure 3:
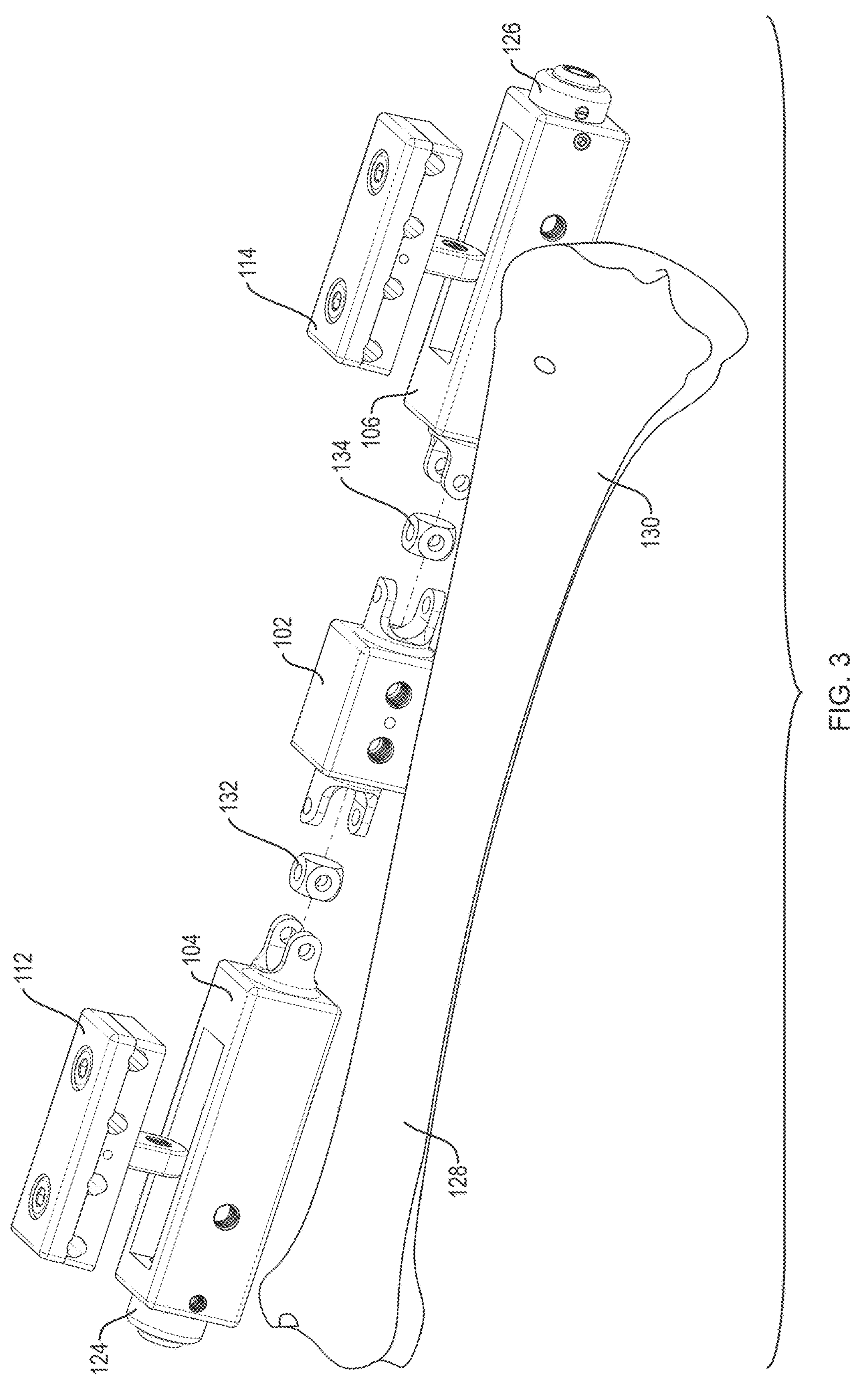
FIG. 3 is an exploded view of the embodiment of FIG. 1.

FIG. 3 is an exploded view of the embodiment of FIG. 1 and shows additional components that are not visible in the view of FIG. 1. A first cross 132 is disposed between the central body 102 and the first base 104, and is part of the first universal joint 108. A second cross 134 is disposed between the central body 102 and the second base 106, and is part of the second universal joint 110.

The first bone attachment base 112 is in sliding communication with the first base 104 and is translated along the longitudinal axis of the first base by adjusting the first axial adjustment screw 124. The second bone attachment base 114 is in sliding communication with the second base 106 and is translated along the longitudinal axis of the second base by adjusting the second axial adjustment screw 126.

Figure 4:
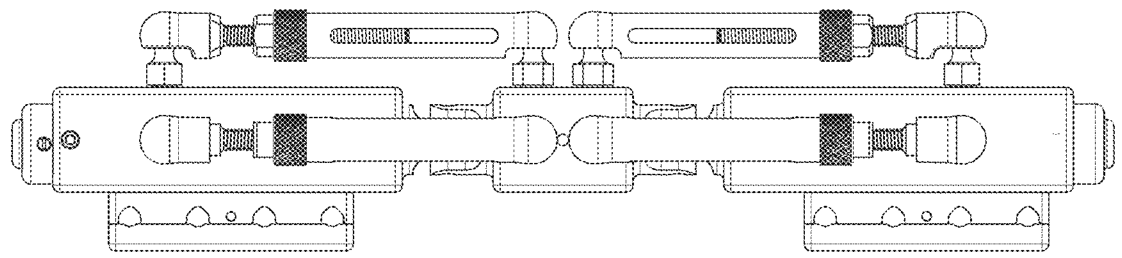
FIG. 4 is a front elevation of the embodiment of FIG. 1.
Figure 5:
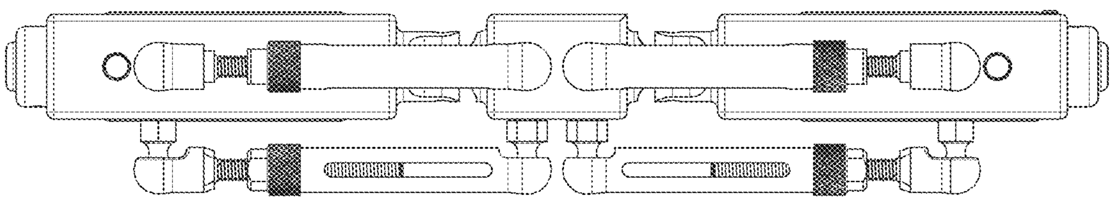
FIG. 5 is a plan view of the embodiment of FIG. 1.
Figure 6:
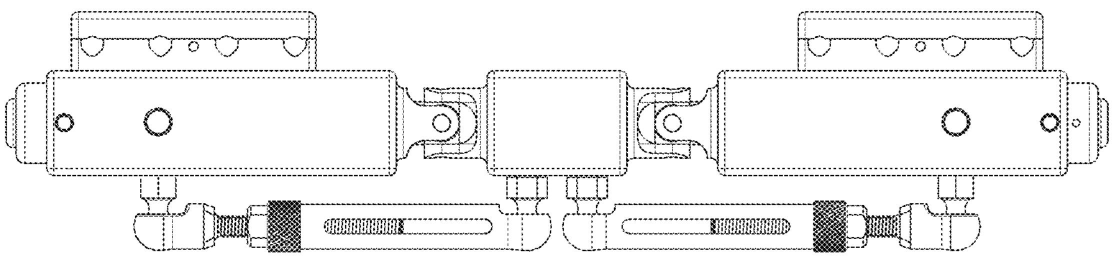
FIG. 6 is a rear elevation of the embodiment of FIG. 1.
Figure 7:
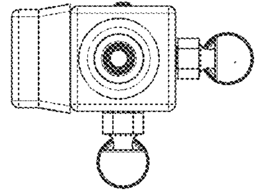
FIG. 7 is a side elevation of the embodiment of FIG. 1.

FIGS. 4-6 show the front elevation, plan view, and rear elevation of the UEF of FIG. 1 respectively. FIG. 7 shows the side elevation.

Figure 8:
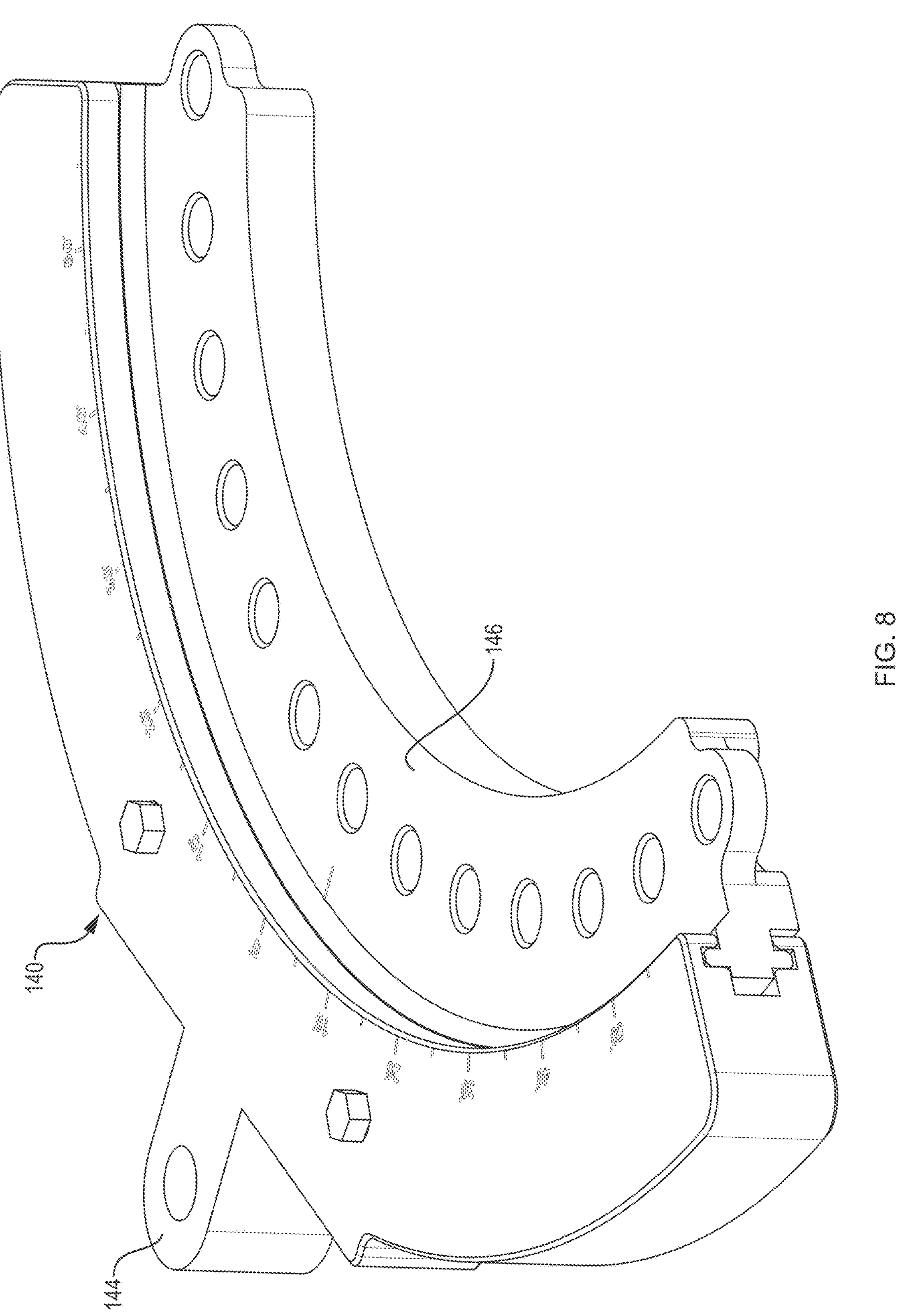
FIG. 8 is a perspective detail view of the rotator of the embodiment of FIG. 2.

FIG. 8 is a perspective view of the rotator assembly 140 of the embodiment of FIG. 2. The rotator assembly 140 comprises a mounting adapter 144 having structure for attaching the rotator assembly to the first base 104 as shown in FIG. 2. A rotating inner part 146 is secured in a rotating relationship along a groove or track in the mounting adapter as shown in FIG. 8. Note the angular gradations on the mounting adapter 144 and the hash mark on the rotating inner part 146 that assists a user in locating the rotating inner part 146 in a desired orientation. Also note the mounting structures in the rotating inner part for adjustably attaching the linking member that is shown in FIG. 2.

Figure 9:
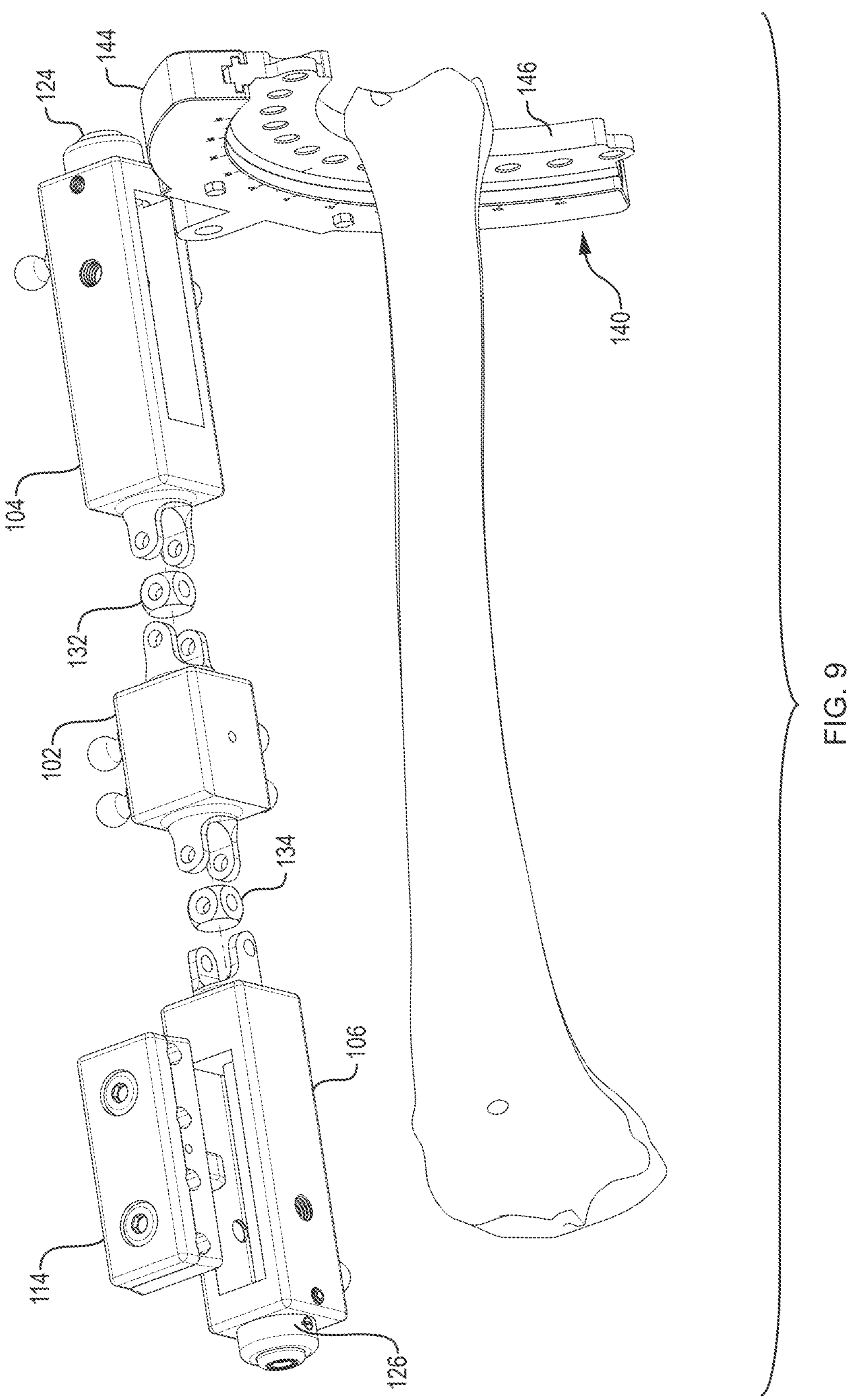
FIG. 9 is an exploded view of the embodiment of FIG. 2.

FIG. 9 is an exploded view of the embodiment of FIG. 2 and shows additional components that are not visible in the view of FIG. 2. Like with the first embodiment, a first cross 132 is disposed between the central body 102 and the first base 104, and is part of the first universal joint 108. A second cross 134 is disposed between the central body 102 and the second base 106, and is part of the second universal joint 110.

The rotator assembly 140 is in sliding communication with the first base 104 and is translated along the longitudinal axis of the first base by adjusting the first axial adjustment screw 124. The second bone attachment base 114 is in sliding communication with the second base 106 and is translated along the longitudinal axis of the second base by adjusting the second axial adjustment screw 126.

Figures 10, 11, 12:
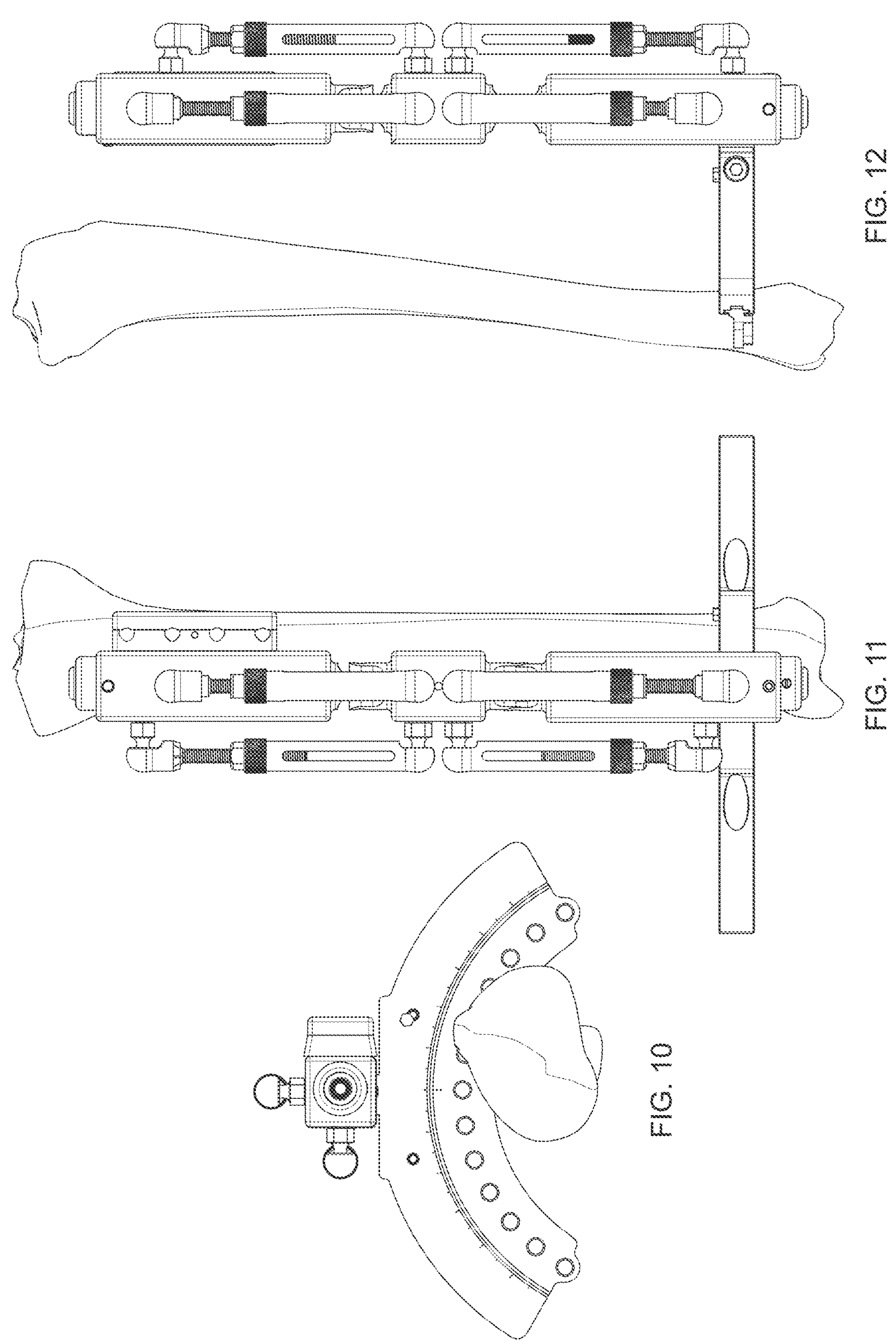
FIG. 10 is a side elevation of the embodiment of FIG. 2.
FIG. 11 is a rear elevation of the embodiment of FIG. 2.
FIG. 12 is a plan view of the rotator assembly of the embodiment of FIG. 2.

FIGS. 10-12 show the side elevation, rear elevation, and plan view of the UEF of FIG. 2 respectively.

Figure 13:
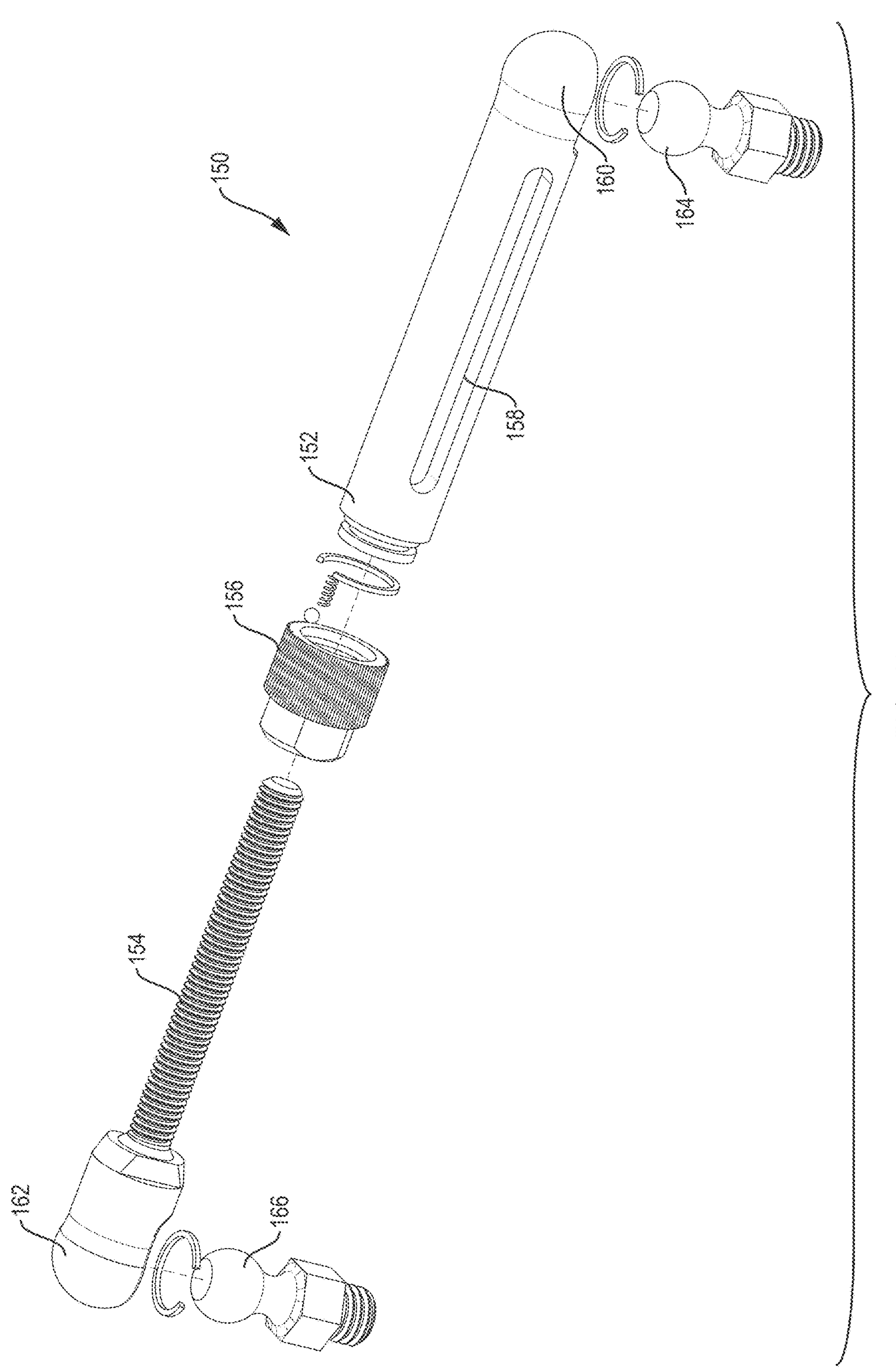
FIG. 13 is an exploded perspective view of an angulation adjustment screw assembly.

FIG. 13 is an exploded perspective view of an angulation adjustment screw 150, and shows the components and details of any of the first through fourth angulation adjustment screw assemblies 116-122. A joint is disposed at the first and second ends of the angulation adjustment screw assemblies, and the particular joint shown in FIG. 13 is a ball and socket joint. The joint could also be a universal joint, not shown. The angulation adjustment screw assembly 150 comprises a barrel 152, a threaded rod 154, and an adjustment nut 156 that engages the barrel 152 and threaded rod 154. Rotating the adjustment nut 156 adjusts the overall length of the angulation adjustment screw assembly. The barrel comprises at least one window 158 through which an operator can see an end of the threaded rod 154, or an indicator structure connected to the threaded rod. Preferably, length gradations are applied to the barrel 152 that assist an operator in adjusting the overall length of the angulation adjustment screw assembly by matching the position of the end of the threaded rod with a desired gradation.

For a ball and socket joint, a first pin receiver 160 is disposed on one end of the barrel 152 and is adapted to receive a first pin 164. A second pin receiver 162 is disposed on one end of the threaded rod 154 and is adapted to receive a second pin 166. As shown in FIG. 1, first and second pins, which are not numbered in FIG. 1, are attached to the central body 102 and one of the first base 104 or the second base 106.

Next, a method to control the movement of an external fixator to correct a bone deformity or reduce a bone fracture of an extremity is presented. The method requires the inverse kinematic control of the kinematic structure, with respect to an arbitrary, user-defined reference point. The solution to the problem is an algorithm, which allows computer-based evaluation and supplies the user with the required settings that achieve desired position and orientation. The solution should also consider the limitations of motion of the given device.

The inputs to the expected algorithm are the dimensions of the external fixator, the location and the orientation of two fractured bone segments, as well as an initial position and orientation and a target position and orientation. The expected output is the set of adjustment settings to change the current position to a desired target position. The settings include, but are not limited to, settings for rotation adjustment screws, axial adjustment screws, and for the rotator assembly. The transition from initial to target position should follow a trajectory with a user-defined number of intermediate steps.

The method includes the two embodiments of the external fixator, the basic version with five degrees of freedom (DOF) as shown in FIG. 1 and the extended version with the full range of six DOF as shown in FIG. 2.

The modeling and simulation of kinematic structures used as manipulators have always been a central issue in the area of robotics, as this forms the basis for both research and the implementation of robotic systems. While the matter is of highly complex nature, the modeling process itself is often more of a necessary but recurrent prerequisite, rather than being of key interest. Especially concerning dynamic systems such as manipulators, the area of robotics has developed several unified methods for their kinematic description and the calculation of dynamic forces. These methods simplify both documentation and implementation of complex linear and non-linear systems. Furthermore, as general requirements in robotics are often of similar nature, these commonly used methods are well-suited for numeric implementation in real-time systems.

Figure 14:
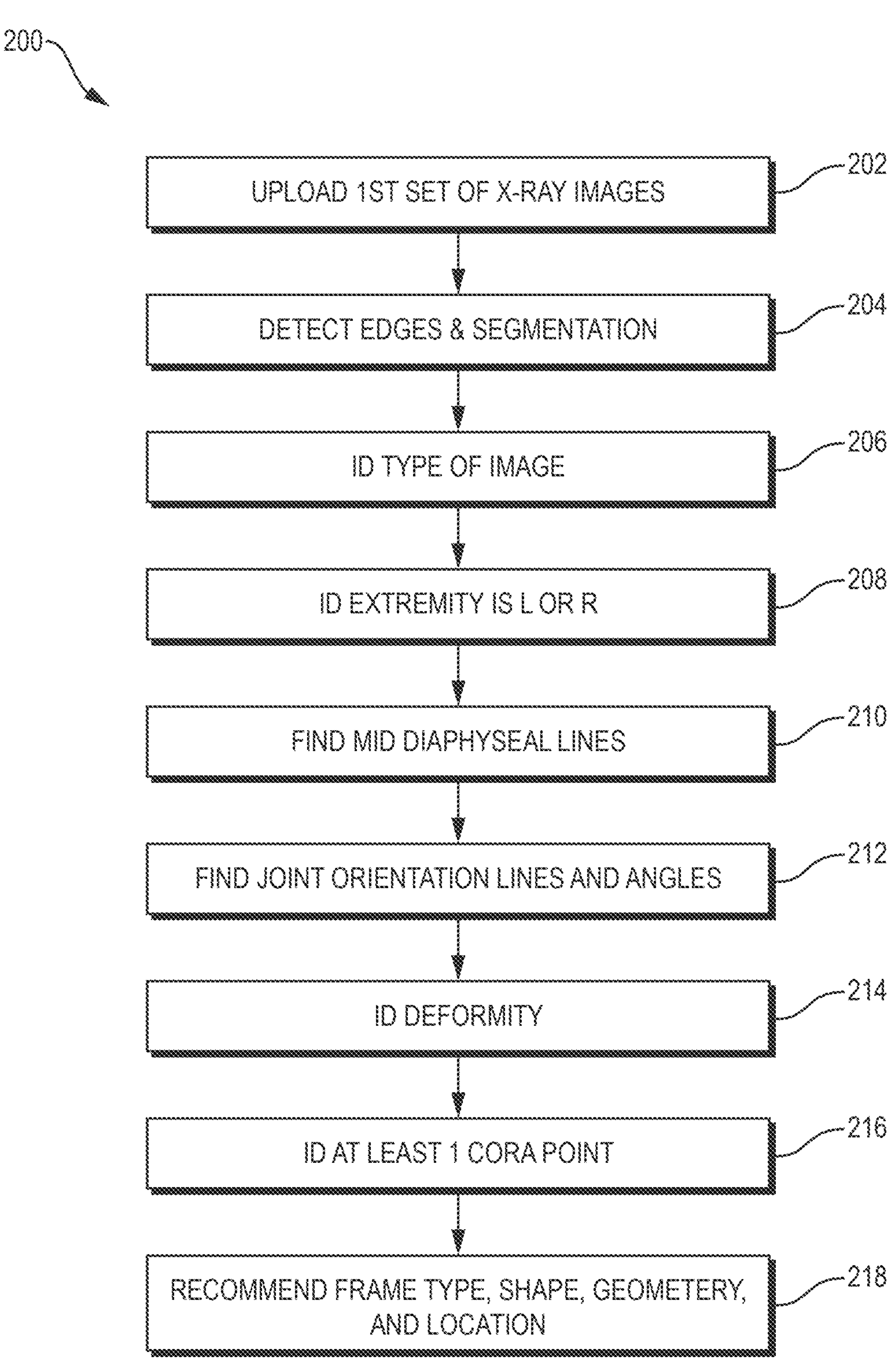
FIG. 14 is a flow chart of a method of correcting a bone deformity or reducing a bone fracture with an external fixator, pre-surgery.

Turning to FIG. 14, a method 200 of correcting a bone deformity or reducing a bone fracture of an extremity with an external fixator comprises the steps of first uploading a first set of x-ray images of the bone deformity taken prior to surgery without the fixator to a computer software program 202. Then, automatically, with the computer software program, characterize the geometry of the bone deformity or bone fracture before surgery. Characterizing the geometry comprises performing the steps of detecting bone segment edges and segmentation 204, identifying whether an x-ray image is a coronal plane image, or a sagittal plane image 206, identifying whether the extremity is a left or right extremity 208, finding mid diaphyseal lines for each bone segment 210, finding joint orientation lines and joint orientation angles 212, identifying the deformity and bone segment positions 214, and identifying at least one cora point 216. The computer software program then recommends a frame type, shape, osteotomy level, and geometry for the bone deformity to be corrected using the external fixator 218. Note that, as used in this specification and in the claims, the term "cora" means "center of rotation of angulation." Also, the methods described in this specification and the claims can be applied to several types of external fixators including without limitation, unilateral, bilateral, and circulator fixators.

Figure 15:
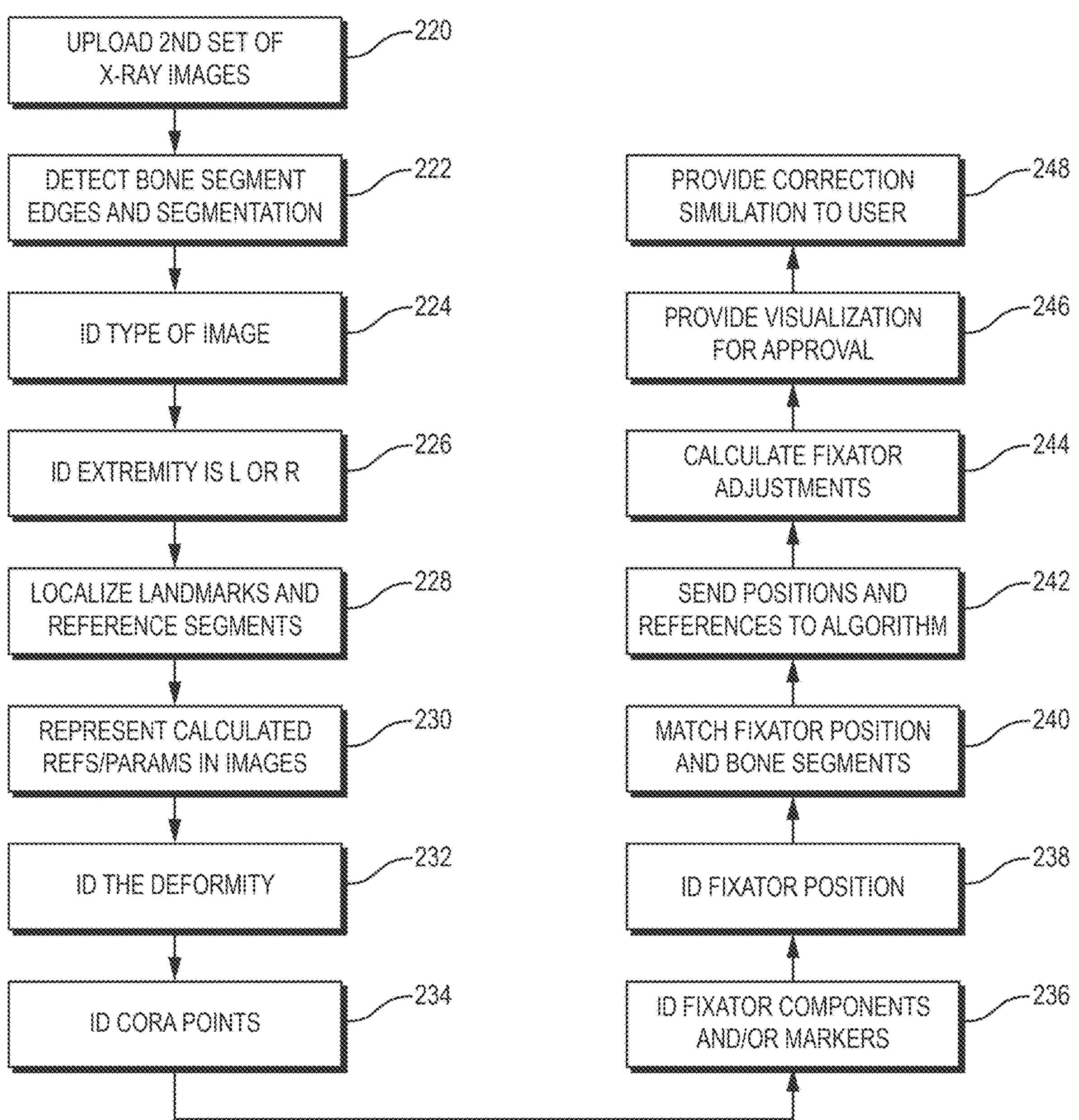
FIG. 15 is a flow chart continuing the method of FIG. 14 post-surgery.

After surgery, the method continues with the steps shown in FIG. 15. The next step is uploading a second set of x-ray images with the fixator taken after surgery to the computer software program 220.

Then, automatically, with the computer software program, characterize the geometry of the bone deformity or bone fracture after surgery. Characterizing the geometry comprises performing the steps of detecting bone segment edges and segmentation 222, identifying whether an x-ray image is a coronal plane image, or a sagittal plane image 224, identifying whether the extremity is a left or right extremity 226, localizing landmarks and reference segments in the coronal plane image and/or the sagittal plane image 228, representing the calculated angles in the coronal plane image and/or in the sagittal plane image 230, identifying the deformity and bone segment positions 232, identifying cora points 234, identifying fixator components and/or markers 236, identifying fixator geometric positions 238, and matching fixator positions and bone segment positions 240. Then the computer software program sends bone segment position parameters and fixator references with necessary correction parameters, such as translation, angulation, distraction/compression and/or rotation requirements entered by a user or surgeon to a correction algorithm of the computer software program 242, calculating fixator adjustments necessary to align bone segments 244, providing visualization of aligned bone segments in two and three dimensions and proposed fixator positions for user approval 246, and providing a correction simulation and/or animation with modeled three dimensional bone and fixator model to a user for correcting the bone deformity with the external fixator 248.

The computer software program can be an artificial intelligence ("AI") application. An input prompt for the AI application can comprise the first set of x-ray images and the second set of x-ray images.

Figure 16:
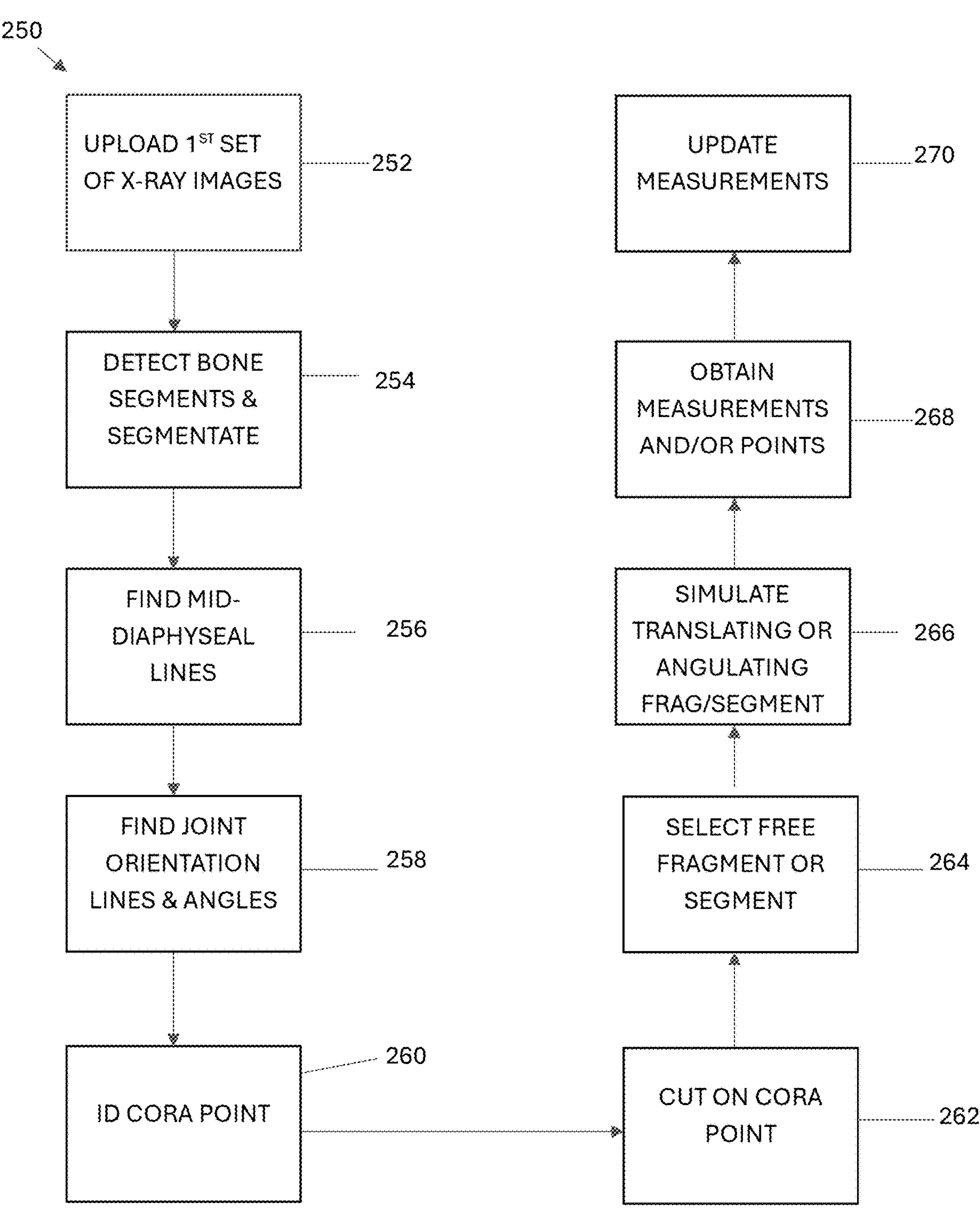
FIG. 16 is a flow chart of a method of correcting a bone deformity or reducing a bone fracture with the assistance of a computer software program.

FIG. 16 is a process flow chart of a method of correcting a bone deformity or reducing a bone fracture of an extremity with an external fixator 250. The method comprises steps starting with uploading a first set of x-ray images of the bone deformity or bone fracture taken prior to surgery without the fixator to a computer software program 252. Then the computer program automatically performs the steps of detecting bone segments and segmentate 254, finding mid-diaphyseal lines for each bone segment 256, finding joint orientation lines and joint orientation angles 258, and identifying at least one cora point or accepting a user input of marking an area and a position of at least one cora point 260. The method continues with a user cutting on the cora point on the area identified by the user or as a result of segmentation representing a bone to simulate an osteotomy 262, selecting a free fragment and/or segment 264, using arrows provided in the computer software program, simulate translating and/or angulating the bone fragment and/or segment 266, obtaining resulting measurements and/or points from the computer software program from the simulated translating and/or angulating to assist the user correcting the bone deformity or reducing the bone fracture 268, and updating measurements according to a motion of the free fragment and/or segment 270.

As used in this specification and in the claims, the computer program automatically performing recited steps includes providing instructions stored on a computer-readable medium that when executed perform those recited steps.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

TABLE OF REFERENCE NUMBERS

| Reference Number | Description |
|---|---|
| 100 | unilateral external fixator assembly |
| 102 | central body |
| 104 | first base |
| 106 | second base |
| 108 | first joint |
| 110 | second joint |
| 112 | first bone attachment base |
| 114 | second bone attachment base |
| 116 | first angulation adjustment screw assembly |
| 118 | second angulation adjustment screw assembly |
| 120 | third angulation adjustment screw assembly |
| 122 | fourth angulation adjustment screw assembly |
| 124 | first axial adjustment screw |
| 126 | second axial adjustment screw |
| 128 | lower bone mockup |
| 130 | upper bone mockup |
| 132 | first cross |
| 134 | second cross |
| 140 | rotator assembly |
| 142 | linking member |
| 144 | mounting adapter |
| 146 | rotating inner part |
| 150 | angulation adjustment screw assembly |
| 152 | barrel |
| 154 | threaded rod |
| 156 | adjustment nut |
| 158 | window |
| 160 | first pin receiver |
| 162 | second pin receiver |
| 164 | first pin |
| 166 | second pin |
| 200 | method of correcting a bone deformity or reducing a bone fracture with an external fixator |
| 202 | upload first set of x-ray images |
| 204 | detect edges and segmentation |
| 206 | identify type of image |
| 208 | identify whether the extremity is left or right |
| 210 | find mid diaphyseal lines |
| 212 | find joint orientation lines and angles |
| 214 | identify the deformity |
| 216 | identify at least one cora point |
| 218 | recommend frame type, shape, geometry, and location |
| 220 | upload second set of x-ray images |
| 222 | detect bone segment edges and segmentation |
| 224 | identify type of image |
| 226 | identify whether the extremity is left or right |
| 228 | localize landmarks and reference segments |
| 230 | represent calculated positions in images |
| 232 | identify the deformity |
| 234 | identify cora points |
| 236 | identify fixator components and/or markers |
| 238 | identify fixator position |
| 240 | match fixator position and bone segments |
| 242 | send positions and references to correction algorithm |
| 244 | calculate fixator adjustments |
| 246 | provide visualization for approval |
| 248 | provide correction simulation to user |
| 250 | method of correcting a bone deformity or reducing a bone fracture |
| 252 | upload first set of x-ray images |
| 254 | detect bone segments and segmentate |
| 256 | find mid-diaphyseal lines |
| 258 | find joint orientation lines and angles |
| 260 | identify cora points |
| 262 | cut on cora point |
| 264 | select free fragment or segment |
| 266 | simulate translating and/or angulating fragment and/or segment |
| 268 | obtain measurements and/or points |
| 270 | update measurements |

The invention claimed is:

1. A method of correcting a bone deformity or reducing a bone fracture of an extremity with an external fixator comprising the steps of:
 uploading a first set of x-ray images of the bone deformity or bone fracture taken prior to surgery without the fixator to a computer software program;
 automatically, with the computer software program, performing the steps of:
  detecting bone segment edges and segmentation;
  identifying whether an x-ray image of the first set of x-ray images is a coronal plane image, or a sagittal plane image;
  identifying whether the extremity is a left or right extremity;
  finding mid diaphyseal lines for each bone segment;
  finding joint orientation lines and joint orientation angles;
  identifying the deformity or fracture and bone segment positions;
  identifying at least one cora point; and
  recommending a frame type, shape, geometry, and position for the bone deformity to be corrected or bone fracture to be reduced using the external fixator;
 uploading a second set of x-ray images with the fixator taken after surgery;
 automatically, with the computer software program, performing the steps of:
  detecting bone segment edges and segmentation;
  identifying whether an x-ray image of the second set of x-ray images is a coronal plane image, or a sagittal plane image;
  identifying whether the extremity is a left or right extremity;
  localizing landmarks and reference segments in the coronal plane image and/or the sagittal plane image;

representing the calculated geometrical positions of bone segments in the coronal plane image and/or in the sagittal plane image;

identifying the deformity or fracture and bone segment positions;

identifying cora points;

identifying fixator components and/or markers;

identifying fixator geometric positions;

matching fixator positions and bone segment positions;

sending bone segment position parameters and fixator references with necessary correction or reduction parameters, the correction or reduction parameters comprising angulation, translation, distraction/compression, and/or rotation requirements that may be entered by user to a correction algorithm of the computer software program;

calculating fixator adjustments necessary to align bone segments;

providing visualization of aligned bone segments in two and three dimensions and proposed fixator positions for user approval; and providing a correction simulation and/or animation with modeled three-dimensional bone and fixator model to a user for correcting the bone deformity or reducing the bone fracture with the external fixator, the computer software program comprising an artificial intelligence application, wherein an input prompt for the artificial intelligence application comprises the first set of x-ray images and the second set of x-ray images.

2. The method of claim 1, the external fixator comprising a unilateral fixator.

3. The method of claim 1, the external fixator comprising a circular fixator.

4. The method of claim 1, the external fixator comprising a bilateral fixator.

5. A method of correcting a bone deformity or reducing a bone fracture with an external fixator comprising the steps of:

a) providing an external fixator comprising:

a central body;

a first base and a second base in operative communication with the central body via respective joints; and angulation adjustment screw assemblies and axial adjustment screw assemblies connected to the central body and the first and second base that adjust the relative positions of the first base and second base;

b) uploading a first set of x-ray images of the bone deformity or bone fracture taken prior to surgery without the fixator to a computer software program;

c) automatically characterizing the geometry of the bone deformity or bone fracture with the computer software program;

d) recommending, using the computer software program, a frame type, shape, and geometry for the bone deformity to be corrected or bone fracture to be reduced using the external fixator;

e) uploading a second set of x-ray images with the fixator taken after surgery;

f) automatically characterizing the geometry of the bone deformity or bone fracture and fixator after surgery with the computer software program;

g) getting direction from a user for planning the correction or reduction, meaning a final relationship between the bone segments, or getting approval from the user for a recommended correction plan or reduction plan by the computer software program;

h) sending the characterized geometry to a correction algorithm or reduction algorithm of the computer software program;

i) calculating fixator adjustments necessary to align bone segments;

j) providing visualization of aligned bone segments in two and three dimensions and proposed fixator position for user approval; and k) providing a correction simulation or reduction simulation and/or animation with modeled three-dimensional bone and fixator model to a user for correcting the bone deformity or reducing the bone fracture with the external fixator, the computer software program comprising an artificial intelligence application, wherein an input prompt for the artificial intelligence application comprises the first set of x-ray images and the second set of x-ray images.

6. The method of claim 5, the external fixator comprising a unilateral fixator.

7. The method of claim 5, the external fixator comprising a circular fixator.

8. The method of claim 5, the external fixator comprising a bilateral fixator.

9. A method of correcting a bone deformity or reducing a bone fracture of an extremity with an external fixator comprising the steps of:

uploading a first set of x-ray images of the bone deformity or bone fracture taken prior to surgery without the fixator to a computer software program;

automatically characterizing the geometry of the bone deformity or bone fracture with the computer software program before surgery; and recommending a frame type, shape, geometry, and position for the bone deformity to be corrected or bone fracture to be reduced using the external fixator;

uploading a second set of x-ray images with the fixator taken after surgery;

automatically characterizing the geometry of the bone deformity or bone fracture and fixator after surgery with the computer software program after surgery;

sending bone segment position parameters and fixator references with necessary correction or reduction parameters, the correction or reduction parameters comprising angulation, translation, distraction/compression, and/or rotation requirements that may be entered by user to a correction algorithm of the computer software program;

calculating fixator adjustments necessary to align bone segments;

providing visualization of aligned bone segments in two and three dimensions and proposed fixator positions for user approval; and providing a correction simulation and/or animation with modeled three-dimensional bone and fixator model to a user for correcting the bone deformity or reducing the bone fracture with the external fixator, the computer software program comprising an artificial intelligence application, wherein an input prompt for the artificial intelligence application comprises the first set of x-ray images and the second set of x-ray images.

10. The method of claim 9, the automatically characterizing the geometry of the bone deformity or bone fracture before surgery comprising the steps of:

detecting bone segment edges and segmentation;

identifying whether an x-ray image of the first set of x-ray images is a coronal plane image, or a sagittal plane image;

identifying whether the extremity is a left or right extremity;

finding mid diaphyseal lines for each bone segment;

finding joint orientation lines and joint orientation angles;

identifying the deformity or fracture and bone segment positions; and identifying at least one cora point;

the automatically characterizing the geometry of the bone deformity or bone fracture and fixator after surgery comprising the steps of:

detecting bone segment edges and segmentation;

identifying whether an x-ray image of the second set of x-ray images is a coronal plane image, or a sagittal plane image;

identifying whether the extremity is a left or right extremity;

localizing landmarks and reference segments in the coronal plane image and/or the sagittal plane image;

representing the calculated geometrical positions of bone segments in the coronal plane image and/or in the sagittal plane image;

identifying the deformity or fracture and bone segment positions;

identifying cora points;

identifying fixator components and/or markers;

identifying fixator geometric positions; and matching fixator positions and bone segment positions.

11. The method of claim 9, the external fixator comprising a unilateral fixator.

12. The method of claim 9, the external fixator comprising a circular fixator.

13. The method of claim 9, the external fixator comprising a bilateral fixator.

14. A method of correcting a bone deformity or reducing a bone fracture with an external fixator comprising the steps of:

uploading a first set of x-ray images of the bone deformity or bone fracture taken prior to surgery without the fixator to a computer software program;

automatically, with the computer software program, performing the steps of:

detecting bone segments and segmentate;

finding mid-diaphyseal lines for each bone segment;

finding joint orientation lines and joint orientation angles; and identifying at least one cora point or accepting a user input of marking an area and a position of at least one cora point;

cutting on the cora point on the area identified by the user or as a result of segmentation representing a bone to simulate an osteotomy;

selecting a free fragment and/or segment;

using arrows provided in the computer software program, simulate translating and/or angulating the bone fragment and/or segment;

obtaining resulting measurements and/or points from the computer software program from the simulated translating and/or angulating to assist the user correcting the bone deformity or reducing the bone fracture; and updating measurements according to a motion of the free fragment and/or segment, the computer software program comprising an artificial intelligence application, wherein an input prompt for the artificial intelligence application comprises the first set of x-ray images.

15. The method of claim 14, the external fixator comprising a unilateral fixator.

16. The method of claim 14, the external fixator comprising a circular fixator or a bilateral fixator.

* * * * *